United States Patent [19]
Greenwald et al.

[11] Patent Number: 5,792,069
[45] Date of Patent: Aug. 11, 1998

[54] METHOD AND SYSTEM FOR THE EXTRACTION OF CARDIAC ARTIFACTS FROM EEG SIGNALS

[75] Inventors: Scott D. Greenwald, Norfolk; Charles P. Smith, Medway, both of Mass.

[73] Assignee: Aspect Medical Systems, Inc., Natick, Mass.

[21] Appl. No.: 773,100

[22] Filed: Dec. 24, 1996

[51] Int. Cl.$^6$ ............................................. A61B 5/05
[52] U.S. Cl. ............................ 600/544; 600/545; 607/45
[58] Field of Search .................... 128/731, 732, 128/691; 607/45, 5, 9; 600/544, 545, 504, 528, 509

[56] References Cited

U.S. PATENT DOCUMENTS

| | | | |
|---|---|---|---|
| 4,407,299 | 10/1983 | Culver | 128/731 |
| 4,846,190 | 7/1989 | John | 128/731 |
| 5,269,302 | 12/1993 | Swartz et al. | 607/45 |
| 5,287,859 | 2/1994 | John | 128/731 |
| 5,458,117 | 10/1995 | Chamoun et al. | 128/734 |
| 5,611,350 | 3/1997 | John | 128/731 |

OTHER PUBLICATIONS

Larsen, L.H. and Prinz, P.N., *Electroencephalography and Clinical Neurophysiology* 79 (1991) 242–244, "EKG artifacts suppression from the EEG".

Sigl, J.C., et al. Abstracts S447, "Quantification of EEG Suppression During Anesthesia: Correlation with Isoflurane Dose and Patient Responsiveness", 1995.

Silver MD, J.M. et al., Abstracts S448, "Amrinone Increase $O_2$ Consumption in Right and Left Ventricles of Normal Canine Hearts", 1995.

*Primary Examiner*—Jennifer Bahr
*Assistant Examiner*—Stephen Huang
*Attorney, Agent, or Firm*—Hale and Dorr LLP

[57] ABSTRACT

The disclosed filter removes cardiac artifacts from signals representative of a patient's cerebral activity. The filter preferably replaces portions of the signal including artifacts with temporally adjacent artifact free portions.

22 Claims, 7 Drawing Sheets

METHOD AND SYSTEM FOR THE EXTRACTION OF CARDIAC ARTIFACTS FROM EEG SIGNALS

FIELD OF THE INVENTION

The present invention relates to an improved filter for filtering signals representative of cerebral activity. More particularly, the present invention relates to a filter for removing cardiac or other artifacts from EEG signals.

BACKGROUND OF THE INVENTION

Neurologists and other health care professionals have been using electroencephalographic (EEG) studies for many years to study brain function, and a wide variety of devices for processing and analyzing EEG signals have been developed. By way of example, U.S. Pat. No. 5,458,117, entitled CEREBRAL BIOPOTENTIAL ANALYSIS SYSTEM AND METHOD, issued to Chamoun et al. on Oct. 17, 1996, which is assigned to the assignee of the present invention, describes a system and method for generating a bispectral index from EEG signals. The bispectral index discussed in that patent is a single time varying number that is generally indicative of a patient's anesthetic state. This bispectral index may be used to effectively monitor the anesthetic state of a patient during a surgical procedure.

One problem with devices that process EEG signals (such as the device disclosed in U.S. Pat. No. 5,458,117) relates to artifacts commonly present in EEG signals. For example, EEG signals frequently include artifacts generated as a result of a cardiac QRS complex, or operation of a pacemaker. The presence of such artifacts can adversely affect the operation of any device used to process the EEG signals. It is therefore an object of the present invention to provide a filter for removing such artifacts from EEG signals.

SUMMARY OF THE INVENTION

These and other objects are provided by an improved filter. The filter receives an input signal representative of a patient's cerebral activity (e.g., an EEG signal) and generates therefrom an artifact free, or reduced artifact, filtered signal. According to one aspect of the invention, the filter removes artifacts from the input signal and replaces the removed portions (that included the artifact) with artifact free portions of the input signal temporally adjacent the removed portions. According to another aspect, the filter replaces the removed portions (that included the artifact) with portions of another input signal.

Still other objects and advantages of the present invention will become readily apparent to those skilled in the art from the following detailed description wherein several embodiments are shown and described, simply by way of illustration of the best mode of the invention. As will be realized, the invention is capable of other and different embodiments, and its several details are capable of modifications in various respects, all without departing from the invention. Accordingly, the drawings and description are to be regarded as illustrative in nature, and not in a restrictive or limiting sense, with the scope of the application being indicated in the claims.

BRIEF DESCRIPTION OF THE FIGURES

For a fuller understanding of the nature and objects of the present invention, reference should be made to the following detailed description taken in connection with the accompanying drawings in which the same reference numerals are used to indicate the same or similar parts wherein.

DETAILED DESCRIPTION OF THE PREFERRED EMBODIMENTS

Figure 1:
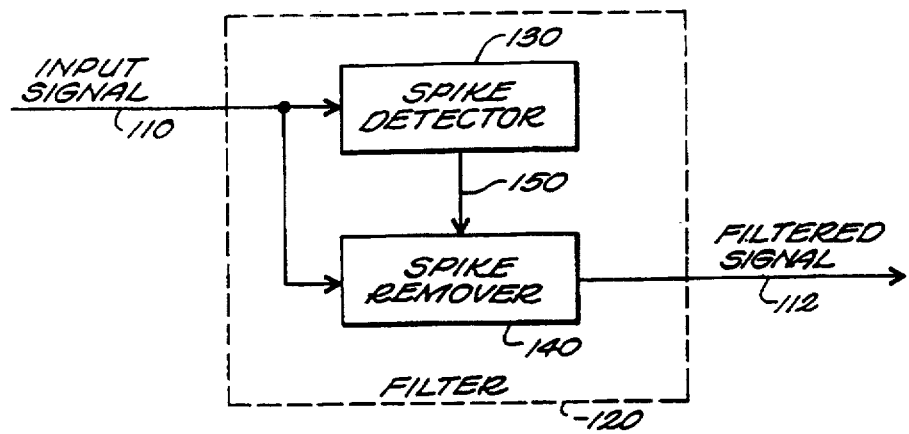
FIG. 1 shows a block diagram of a ECG and pacer artifact filter constructed according to the invention.

FIG. 1 shows a block diagram of a filter 120 constructed according to the invention. Filter 120 receives an input signal 110 representative of cerebral activity of a patient (not shown) and generates therefrom a filtered signal 112. The input signal 110 may be, for example, an EEG signal generated in known fashion by one or more EEG electrodes, or alternatively, by an amplifier or other known EEG processing components. The filtered signal 112 generated by filter 120 may be applied to any device used to process EEG signals (e.g., such as a bispectral index generator of the type disclosed in the above-referenced U.S. Pat. No. 5,458,117). As will be discussed in greater detail below, the filtering provided by filter 120 may improve the performance of any device used to process signals representative of cerebral activity.

In its general form, filter 120 includes a spike detector 130 and a spike remover 140. The input signal 110 is applied to spike detector 130 and spike remover 140. Spike detector 130 generates an output signal 150 that is applied to spike remover 140. The latter generates the filtered signal 112 in response to the input signal 110 and the output signal 150.

In operation, spike detector 130 detects the presence of artifacts in input signal 110 and generates the output signal 150 so that it represents the temporal location of the artifacts in input signal 110. When the input signal 110 does not include an artifact (as indicated by the output signal 150), spike remover 140 generates the filtered signal 112 so that it is substantially equal to the input signal 110. However, when the input signal 110 includes an artifact (as indicated by the output signal 150), spike remover 140 generates the corresponding portion of the filtered signal 112 by setting that portion equal to an artifact free portion of the input signal 110 temporally adjacent the portion of the input signal 110 that included the artifact.

As will be discussed in greater detail below, filter 120 is preferably implemented as a digital filter. Since most frequency components of interest in EEG signals are below sixty Hertz (Hz), sample rates of above 120 Hz satisfy the Nyquist criteria and a preferred sampling rate for use with filter 120 is 128 Hz. Most components of filter 120 preferably process their relevant signals in successive temporal segments referred to as epochs. An epoch of a single signal includes a set of N data points $x_i$ for all integers i from one to N. Different components within filter 120 may use epochs of different lengths (e.g., one second or two second epochs). With the preferred sample rate of 128 Hz, each single second epoch of data includes 128 data points.

In one preferred embodiment, filter 120 is implemented as an ECG and pacer artifact filter. In this embodiment, input signal 110 is an EEG signal and filter 120 processes the EEG signal 110 to remove ECG and pacer artifacts from the filtered signal 112. ECG and pacer artifacts are cardiac artifacts in that they relate to the heart. ECG artifacts are artifacts that arise naturally from the action of the heart muscle (i.e., the electrocardiogram QRS complex). Pacer artifacts arise from electrical instruments used to control the rhythm of the heart (e.g., pacemakers). As is well known, the conductivity of the body often causes these cardiac artifacts to appear in measured EEG signals. Presence of these artifacts in the EEG signals may interfere with the operation of processing components such as a bispectral index generator, so filter 120 detects and removes these artifacts.

Since ECG and pacer artifacts often occur with such a high frequency (e.g., 120 beats per minute), simply detecting and removing the portions of the EEG signal including those artifacts may leave insufficient data for processing components such as a bispectral index generator to process. So, filter 120 preferably generates the filtered signal by (1) removing portions of the EEG signal 110 that include ECG or pacer artifacts, and by (2) replacing the removed portions of data with original (artifact free) data in portions of the EEG signal 110 temporally adjacent the removed portions. Replacing the removed portions of data in this fashion insures that the resulting filtered signal includes sufficient data for processing components such as a bispectral index generator to accurately process. Since the spectral content of temporally adjacent portions of an EEG signal tend to be similar, replacing deleted portions of the EEG signal with temporally adjacent (artifact free) portions does not significantly alter the spectral content of the filtered signal and therefore does not adversely affect the processing provided by subsequent processing components.

Figure 2:
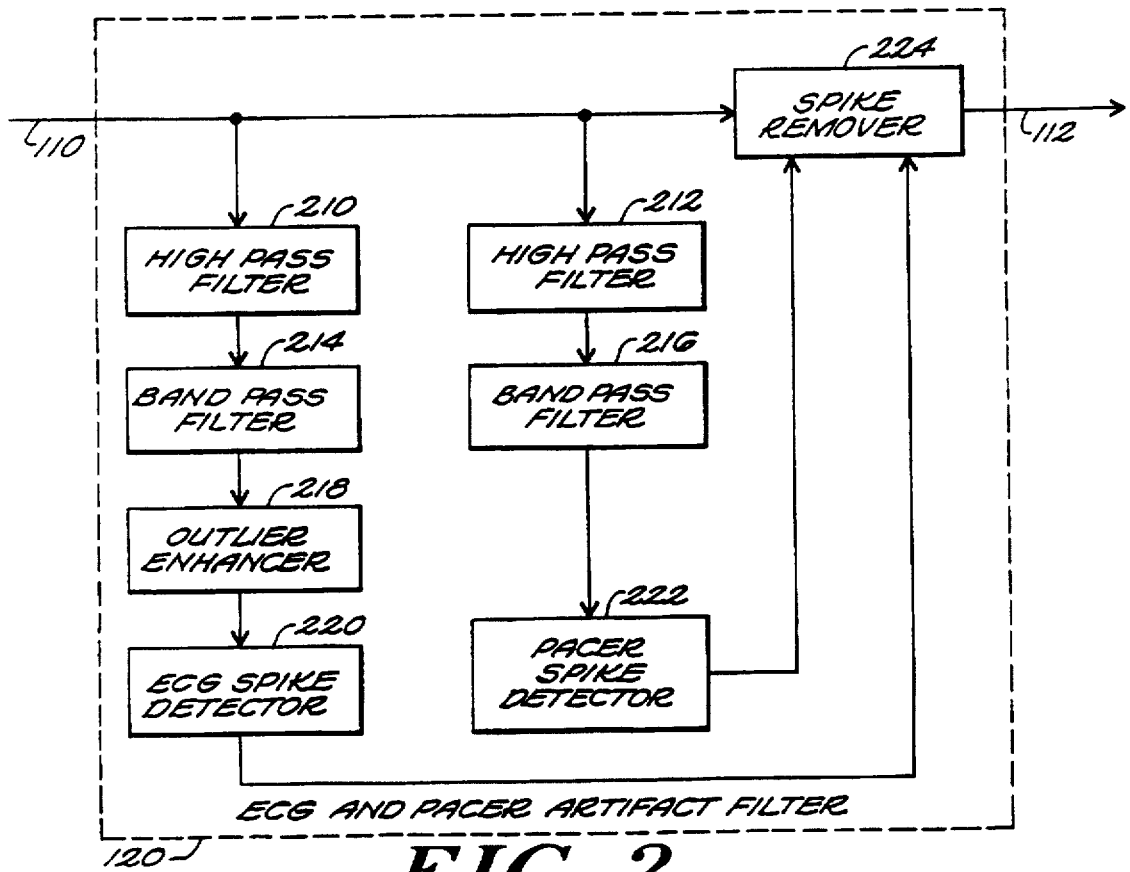
FIG. 2 shows a block diagram of a preferred embodiment of the ECG and pacer artifact filter shown in FIG. 1.

FIG. 2 shows a detailed block diagram of a preferred embodiment of the ECG and pacer artifact filter 120 constructed according to the invention. Filter 120 includes two high pass filters 210, 212; two band pass filters 214, 216; an outlier enhancer 218; an ECG spike detector 220; a pacer spike detector 222; and a spike remover 224. The EEG signal 110 is applied to high pass filters 210, 212, and to spike remover 224. High pass filters 210 and 212 filter the EEG signal 110 and thereby generate output signals that are applied to band pass filters 214 and 216, respectively. Band pass filters 214 and 216 filter the signals received from high pass filters 210 and 212, respectively, and apply the resulting signals to outlier enhancer 218 and pacer spike detector 222, respectively. Outlier enhancer 218 receives the signal from band pass filter 214 and generates therefrom a signal that is applied to ECG spike detector 220. ECG spike detector 220 and pacer spike detector 222 each generate an output signal and these signals are both applied to spike remover 224. The latter generates the filtered signal 112.

Figure 3A:
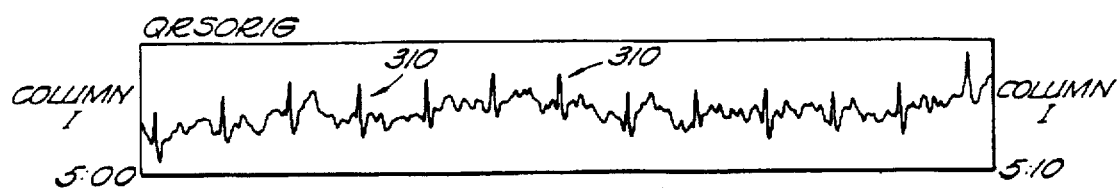
FIGS. 3A-F show graphs of amplitude versus time of signals that illustrate the operation of the filter shown in FIG. 2.
Figure 3B:
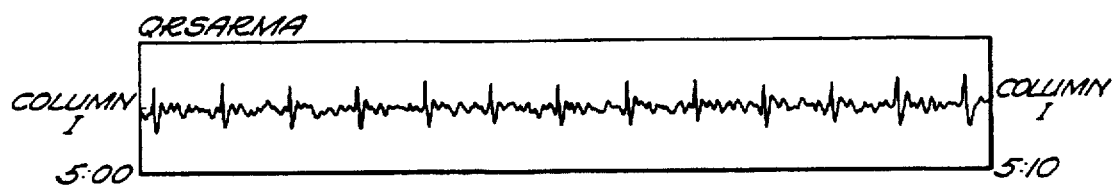

In operation, high pass filter 210, band pass filter 214, outlier enhancer 218, and ECG spike detector 220 cooperatively operate to locate ECG artifacts in the EEG signal 110. FIGS. 3A-3E show graphs of amplitude versus time of signals that illustrate the operation of filters 210, 214, outlier enhancer 218, and ECG spike detector 220. FIG. 3A shows an example of an EEG signal 110 received by high pass filter 210 that includes regularly occurring ECG artifacts some of which are indicated at 310. High pass filter 210 filters this EEG signal to remove low frequency EEG and artifact, such as baseline wander, which may arise, for example, from slowly varying electrode interface characteristics or respiratory cycle related movement. FIG. 3B shows a graph of the output signal generated by high pass filter 210 and applied to band pass filter 214 in response to the signal shown in FIG. 3A. High pass filter 210 is preferably characterized by a high pass cutoff frequency that is selected high enough to effectively remove baseline wander and low enough to pass the ECG artifacts. One preferred value for the high pass cutoff frequency is 5 Hz. Filter 210 may be implemented for example as a first order Auto Regressive first order Moving Average $|ARMA(1,1)|$ filter. In one preferred embodiment, filter 210 is a digital filter characterized by a transfer function shown in the following Equation (1).

$$y_i = a_1 y_{i-1} + \sum_{j=0}^{1} b_j x_{i-j} \quad (1)$$

In Equation (1), $x_i$ represents the current unfiltered sample of the EEG signal applied to the input of filter 210, and $y_i$ and $y_{i-1}$ represent the current and previous samples of the output signal generated by filter 210. In one preferred embodiment, the filter coefficients $a_1$, $b_0$, and $b_1$, are equal to 0.72338247, 1.0, and −1.0, respectively.

Figure 3C:

FIG. 3C shows a graph of an output signal generated by band pass filter 214 in response to the signal shown in FIG. 3B. Band pass filter 214 is characterized by a pass band that is preferably selected so as to accentuate the "spiky" components of the ECG artifacts (as shown in FIG. 3C) and to thereby facilitate their subsequent detection. One preferred range for the pass band of filter 214 is 18–42 Hz. In one preferred embodiment, band pass filter 214 is implemented as a digital pseudo-matched finite impulse response (FIR) filter (i.e., piece-wise linear "complex") filter and is characterized by a transfer function given by the following Equation (2).

$$y_i = \sum_{j=0}^{8} b_j x_{i-j} \quad (2)$$

In one preferred embodiment, the filter coefficients $b_0$ through $b_8$ are selected as follows:

$b_0 = -0.00151596411$ $b_1 = -0.15759821$ $b_2 = -1.1960189$ $b_3 = 0.086164385$ $b_4 = 2.5379448$ $b_5 = 0.086164385$ $b_6 = -1.1960189$, $b_7 = -0.15759821$ $b_8 = -0.00151596411$

Figure 3D:
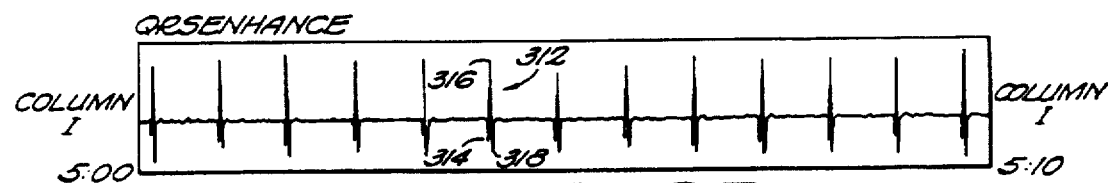

FIG. 3D shows a graph of an output signal generated by outlier enhancer 218 in response to the signal shown in FIG. 3C. As shown in FIG. 3D, outlier enhancer 218 accentuates the ECG artifact and suppresses the rest of the signal. Outliers in the signal generated by band pass filter 214 (e.g., data points that deviate significantly from the mean value of the signal) are generally part of the ECG artifact. Outlier enhancer 218 preferably increases the value of outlying data points and decreases the value of other data points to facilitate subsequent artifact detection. Outlier enhancer 218 preferably uses outlier removal methods described below and in L. H. Larson and P. N. Prinz, "EKG Artifacts Suppression from the EEG", Electroenceph. Olin. Neurophys. 79 (1991) pp. 241–244.

Outlier enhancer 218 preferably processes the signal received from band pass filter 214 in single second epochs. The outlier enhancer 218 processes the N data points $x_i$ in one epoch and then processes the N data points in the next epoch of data. In one preferred embodiment, outlier enhancer 218 processes each epoch of data by first adjusting the data so that it has a mean of zero. To perform this zero mean adjustment, outlier enhancer 218 first generates the mean of the data in the epoch according to the following Equation (3).

$$\overline{X} = \frac{1}{N} \sum_{i=1}^{N} x_i \quad (3)$$

Outlier enhancer 218 then subtracts the mean from every data point in the epoch to generate a set of "zero mean data points" $\hat{x}_i$ according to the following Equation (4).

$$\hat{x}_i = x_i - \overline{X} \quad (4)$$

Outlier enhancer 218 then generates the standard deviation (or the RMS power) of all the zero mean data points in the epoch according to the following Equation (5).

$$RMS = \sqrt{\frac{1}{N} \sum_{i=1}^{N} \hat{x}_i^2} \quad (5)$$

Outlier enhancer 218 then generates data points $x'_i$ for a line that represents the "least squares fit" to the zero mean data points $\hat{x}_i$. The data points $x'_i$ may be generated according to the following Equation (6).

$$x'_i = a + bi \quad (6)$$
where
$$a = -b\overline{i}$$

$$b = \frac{\sum_{i=1}^{N} \hat{x}_i (i - \overline{i})}{\sum_{i=1}^{N} (i - \overline{i})^2}$$

$$\overline{i} = \frac{1}{N} \sum_{i=1}^{N} i$$

Most zero mean data points $\hat{x}_i$ will not deviate significantly from the least squares fit data points $x'_i$ unless the zero mean data point $\hat{x}_i$ is an outlier (or part of an ECG artifact). The data points $x'_i$ may therefore be referred to as "predicted data points". The predicted data points $x'_i$, the zero mean data points $\hat{x}_i$, and the RMS value may then be used to generate a set of data points x_out$_i$ according to the following Equation (7).

$$x\_out_i = x'_i + 7 \cdot RMS \cdot f\left(\frac{\hat{x}_i - x'_i}{7 \, RMS}\right) \quad (7)$$

where
$f(z) = z(1 - z^2)(1 - z^2)$ if $|z| < 1$
$f(z) = 0$ otherwise

The function f(Z) is selected so that the operation of Equation (7) tends to set the value of the data points x_out$_i$ to the predicted value $x'_i$ plus a scaled difference of the predicted and zero mean values. If however, the original data point $x_i$ was an outlier, the corresponding data points x_out$_i$ is set equal to the predicted value $x'_i$ (see the equation above). Outlier enhancer 218 then generates its final output data points by subtracting the data points received from band pass filter 214 from the corresponding data points x_out$_i$.

Figure 4:
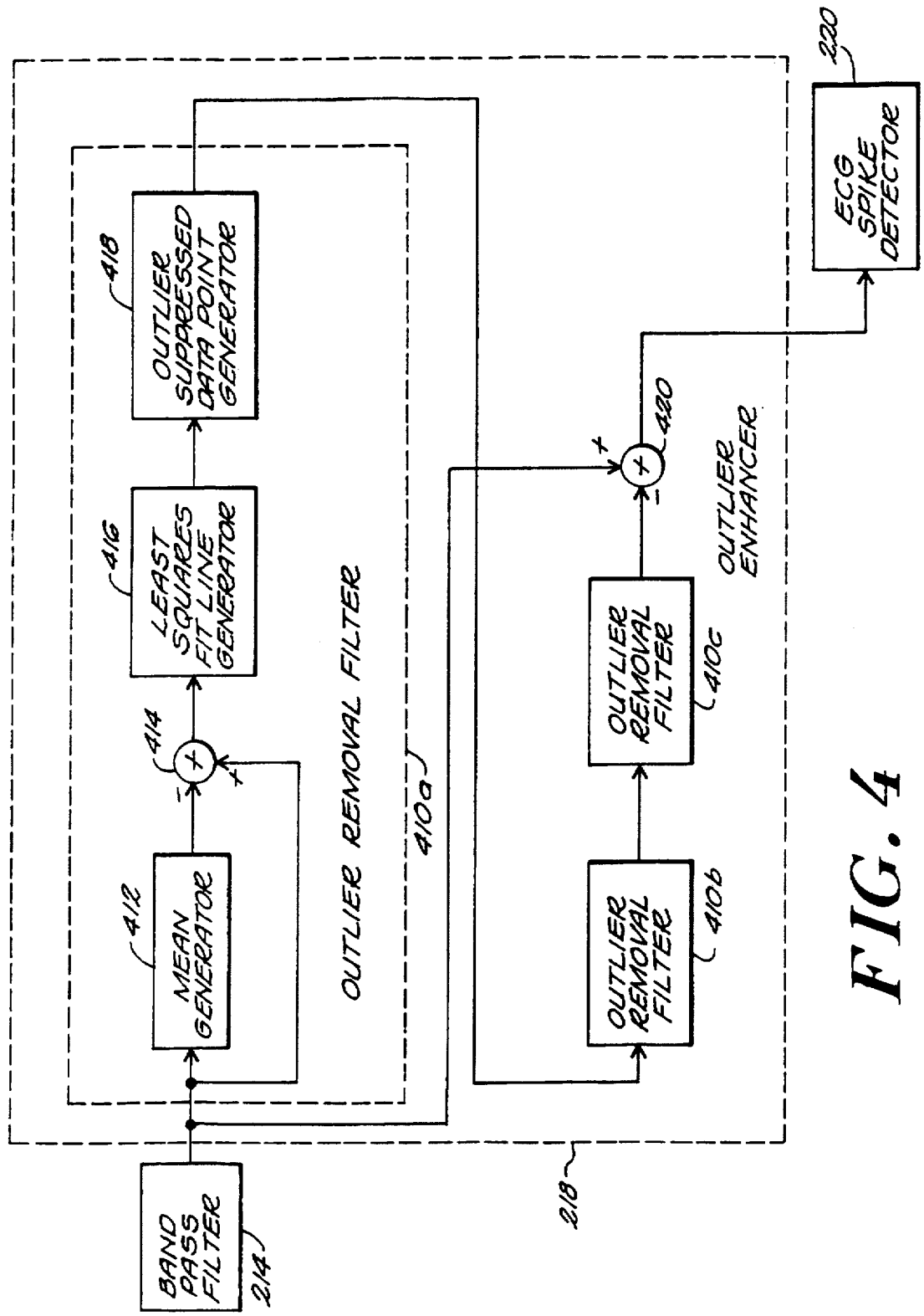
FIG. 4 shows a block diagram of a preferred embodiment of the outlier enhancer shown in FIG. 2.

FIG. 4 shows a block diagram of a preferred embodiment of outlier enhancer 218 that includes a cascade of three outlier removal filters 410a, 410b, and 410c, and a subtractor 420. The output signal generated by band pass filter 214 is applied to filter 410a and to the positive input of subtractor 420. Filter 410a receives the signal from band pass filter 214 and generates therefrom an output signal that is applied to filter 410b, which in turn generates an output signal that is applied to filter 410c. The latter generates an output signal that is applied to a negative input of subtractor 420 which in turn generates the output signal of outlier enhancer 218 that is applied to ECG spike detector 220 (shown in FIG. 2). FIG. 4 shows a detailed block diagram of outlier removal filter 410a, and filters 410b and 410c are constructed in a substantially similar fashion. Filter 410a includes a mean generator 412, a subtractor 414, a least squares fit generator 416, and an outlier suppressed data point generator 418.

In operation, mean generator 412 generates the mean of all the data points in an epoch according to the above Equation (3) and applies the mean to a negative input of subtractor 414. Subtractor 414 then generates the zero mean data points $\hat{x}_i$ according to the above Equation (4) by subtracting the mean from the original data points and applies the zero mean data points to least squares fit line generator 416. Least squares fit line generator 416 then generates the least squares fit line data points $x'_i$ according to the above Equation (6). Outlier suppressed data point generator 418 then generates the outlier suppressed data points x_out$_i$ according to the above Equations (5) and (7). Outlier filters 410b and 410c then each repeat in succession the steps of zero mean generation, least squares line fitting, and outlier suppressed data point generation so that the data points generated by filter 410c significantly suppress the ECG artifacts. Subtractor 420 then enhances the ECG artifacts by subtracting the data points generated by filter 410c from the data points generated by band pass filter 214. Other embodiments of outlier enhancer 218 could of course include more than or less than three outlier removal filters.

Figure 3E:
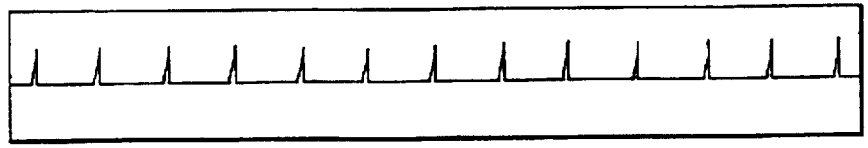

FIG. 3E shows a graph of the output signal generated by ECG spike detector 220 in response to the signal received from outlier enhancer 218 and illustrated in FIG. 3D. The output signal generated by ECG spike detector 220, which is applied to spike remover 224, indicates the location of ECG artifacts in the EEG signal 110. In the signal illustrated in FIG. 3E, a low value indicates the absence of an ECG artifact, and a high value indicates the location of an ECG artifact.

Filtered ECG artifacts are generally characterized by relatively large steep-sloped segments alternating (i.e., rising and falling) within a predetermined period. For example, ECG artifact 312 (shown in FIG. 3D) includes a steep negative transition from a value near zero to the negative data point 314, followed by a steep positive transition (across zero) to the positive data point 316, followed by a steep negative transition (across zero) to the negative data point 318, finally followed by a steep positive transition to a value near zero. ECG spike detector 220 preferably detects the presence, and determines the locations, of ECG artifacts by identifying zero-crossings (i.e., locations where the signal transitions from a negative value "across zero" to a positive value, or transitions from a positive value "across zero" to a negative value).

In one embodiment, ECG spike detector 220 generates an output signal indicative of the presence of an ECG artifact whenever the detector locates M zero-crossings in the signal generated by outlier enhancer 218 in a time interval of duration $T_1$, where M is greater than or equal to two and less than or equal to four, and where $T_1$ is equal to approximately 200 ms. Preferably, ECG spike detector 220 uses a threshold $ZCTR_1$ to determine when zero crossings occur. That is, detector 220 will consider any transition from $-ZCTR_1$ to $ZCTR_1$ or from $ZCTR_1$ to $-ZCTR_1$ in the signal received from outlier enhancer 218 as a zero crossing. Requiring the magnitude of the zero crossings to be greater than a threshold prevents zero crossings caused by small amounts of random noise from being considered as ECG artifacts. One preferred value for the threshold $ZCTR_1$ is 8.032 µV, however, as those skilled in the art will appreciate, this threshold is preferably appropriately varied depending on the type of EEG electrodes used as well as other well known factors. In any particular implementation of filter 120, the threshold $ZCTR_1$ is preferably empirically selected so that it reliably distinguishes actual ECG artifacts from noise.

The ECG spike detector 220 also preferably uses other criteria to prevent detection of an ECG artifact even if M zero crossings greater than $ZCTR_1$ are present in an interval of duration $T_1$. These additional criteria are selected to prevent noise from being detected as an ECG artifact. For example, if spike detector 220 detects five or more zero crossings greater than a second threshold $ZCTR_2$ (i.e., transitions from $-ZCTR_2$ to $ZCTR_2$ or from $ZCTR_2$ to $-ZCTR_2$) in the signal generated by outlier enhancer 218 in an interval of duration $T_2$, then spike detector 220 will generate an output signal indicative of the absence of an ECG artifact. Preferably, the second threshold $ZCTR_2$ is less than the first threshold $ZCTR_1$, and one preferred value for the second threshold $ZCTR_2$ is approximately equal to 3.02727 µV. The second duration $T_2$ is preferably longer than the first duration $T_1$ and one preferred value for the second duration is about half of a second. ECG spike detector 220 also preferably generates an output signal indicative of the absence of an ECG artifact if there is one very large excursion (e.g., greater than 100 µV) of the signal generated by outlier enhancer 218 within an interval of about half of a second. This prevents electrosurgical noise from being detected as ECG artifacts.

Figure 5A:
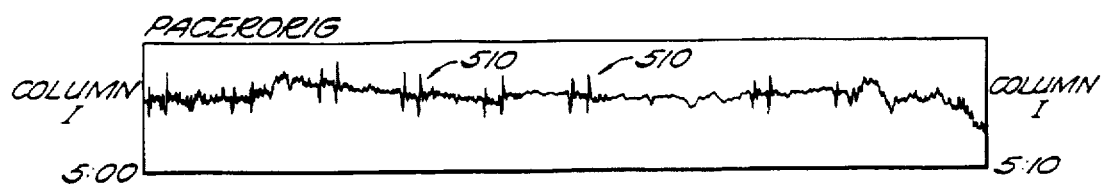
FIGS. 5A-E show graphs of amplitude versus time of signals that illustrate the operation of the filter shown in FIG. 2.
Figure 5B:

As discussed above, high pass filter 210, band pass filter 214, outlier enhancer 218, and ECG spike detector 220 cooperatively operate to locate ECG artifacts in the EEG signal 110. In a similar fashion, high pass filter 212, band pass filter 216, and pacer spike detector 222 cooperatively operate to locate pacer artifacts in the EEG signal 110. FIGS. 5A–5D show graphs of amplitude versus time of signals that illustrate the operation of filters 212, 216, and of pacer spike detector 222. FIG. 5A shows an example of an EEG signal 110 received by high pass filter 212 that includes regularly occurring pacer artifacts some of which are indicated at 510. High pass filter 212 preferably filters this EEG signal to remove low frequency baseline wander. FIG. 5B shows a graph of the output signal generated by high pass filter 212 and applied to band pass filter 216 in response to the signal illustrated in FIG. 5A. High pass filter 212 is preferably characterized by a high pass cutoff frequency that is selected high enough to effectively remove baseline wander and low enough to pass the pacer artifacts. One preferred value for the high pass cutoff frequency for filter 212 is 20 Hz. Filter 212 may be implemented as an ARMA(1,1) filter characterized by the transfer function shown in the above Equation (1), where the filter coefficients $a_1$, $b_0$, and $b_1$, are given by –0.48672403, 1.0, and –1.0, respectively.

Figure 5C:
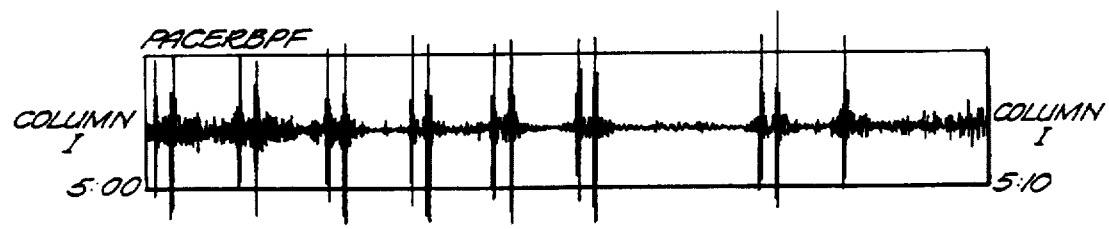

Band pass filter 216 is preferably selected to accentuate the spiky portions of the pacer artifacts. Band pass filter 216 may be implemented using a filter that is identical to the above discussed band pass filter 214. FIG. 5C shows the output signal generated by band pass filter 216 in response to the signal received from high pass filter 212 and illustrated in FIG. 5B.

Figure 5D:
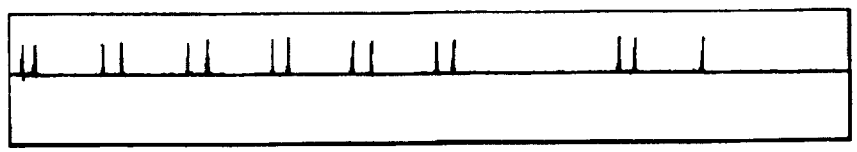

Pacer spike detector 222 generates an output signal that illustrates the presence or absence of pacer artifacts in the EEG signal 110. FIG. 5D shows the output signal generated by pacer spike detector 222 in response to the signal received from band pass filter 216 and illustrated in FIG. 5C. In the illustrated signal, high values indicate the location of pacer artifacts and low values illustrate the absence of pacer artifacts.

Pacer spike detector 222 preferably generates its output signal by cross-correlating the signal received from band pass filter 216 with predetermined templates. Whenever any of the cross-correlations exceeds a predetermined threshold, spike detector 222 generates an output signal indicative of the presence of a pacer artifact and at all other times spike detector 222 generates an output signal indicative of the absence of a pacer artifact. A set of three preferred templates for use with pacer spike detector 222 is shown below.

TEMPLATE1=1,1,1,1,1,1,1,1,1,1,1,1,1,0,–5,0,11,0,–5,0,1, 1,1,1,1,1,1,1,1,1,1,1

TEMPLATE2=1,1,1,1,1,1,1,1,1,1,1,1,1,0,–5,11,0,–5,0,1,1, 1,1,1,1,1,1,1,1,1,1

TEMPLATE3=1,1,1,1,1,1,1,1,1,1,1,1,1,0,–5,0,11,–5,0,1, 1,1,1,1,1,1,1,1,1,1

Pacer spike detector 222 preferably generates cross-correlation functions for each of the three templates shown above according to a function of the "lag" or time shift between the template and the data in the epoch. The cross-correlation function ρ(r) is preferably generated according to the following Equation (8).

$$\rho(r) = \frac{R_{xy}(r)}{\sqrt{R_x(0)}\sqrt{(R_y(0))}} \quad (8)$$

where $$R_{xy}(r) = \frac{1}{N-r}\sum_{i=1}^{N-r} x_i y_{i+r}$$

$$R_x(0) = \frac{1}{N}\sum_{i=1}^{N} x_i^2$$

$$R_y(0) = \frac{1}{N}\sum_{i=1}^{N} y_i^2$$

In the above Equation (8), $x_i$ represents data points in the signal received from band pass filter 216, and $y_i$ represents data points in one of the three templates shown above, and N is the number of data points in an epoch.

When generated according to Equation (8), the magnitude of cross-correlation functions ρ(r) will have values that range between zero and one. Pacer spike detector 222 preferably generates an output signal indicative of the location of a pacer artifact wherever the cross-correlation function ρ(r) for TEMPLATE1 is greater than a first threshold $THR_1$ and also preferably generates an output signal indicative of the location of a pacer artifact wherever the cross-correlation function ρ(r) for TEMPLATE2 or TEMPLATE3 is greater than a second threshold $THR_2$. Preferred values for $THR_1$ and $THR_2$ are 0.85 and 0.75, respectively, although those skilled in the art will appreciate that other values for the threshold and other templates could also be used.

In summary, high pass filter 210, band pass filter 214, outlier enhancer 218, and ECG spike detector 220 cooperatively operate to identify the location of ECG artifacts in the EEG signal 110, and high pass filter 212, band pass filter 216, and pacer spike detector 222 cooperatively operate to identify the location of pacer artifacts in the EEG signal 110. These components (i.e., high pass filters 210, 212, band pass filters 214, 216, outlier enhancer 218, ECG spike detector 220, and pacer spike detector 222) represent one preferred embodiment of the spike detector 130 (shown in FIG. 1) of filter 120. Spike remover 224 then uses the signals generated by ECG spike detector 220 and pacer spike detector 222 to remove the ECG and pacer artifacts from the EEG signal 110. While high pass filters 210, 212, band bass filters 214, 216, outlier enhancer 218, and ECG and pacer spike detectors 220, 222 represent a preferred embodiment for detecting the presence and location of ECG and pacer artifacts, those skilled in the art will appreciate that spike remover 224 may be used with other filters that detect the presence of ECG and pacer artifacts or of other artifacts. For example, while pacer spike detector 222 has been discussed in connection with templates and correlation functions, those skilled in the art will appreciate that spike detector 222 could also operate using zero crossing detection schemes similar to the one discussed above in connection with ECG spike detector 220 and tuned to detect pacer artifacts. Similarly, ECG spike detector 220 could operate using appropriate templates and correlation functions rather than by detecting zero crossings.

EEG signal 110 and the signals generated by ECG spike detector 220 and pacer spike detector 222 are received by spike remover 224. Spike remover 224 generates the filtered signal so that it is equal to the EEG signal 110 when the output signals from spike detectors 220 and 222 indicate an absence of ECG and pacer artifacts. When spike detectors 220 and 222 indicate the presence of an ECG or a pacer artifact, spike remover 224 generates the filtered signal by replacing the portion of the EEG signal including the artifact with artifact free data in the EEG signal that is temporally adjacent to the portion including the artifact. Spike remover 224 also preferably filters the signal so that the replaced portions fit smoothly into the original artifact free portions.

Figure 6:
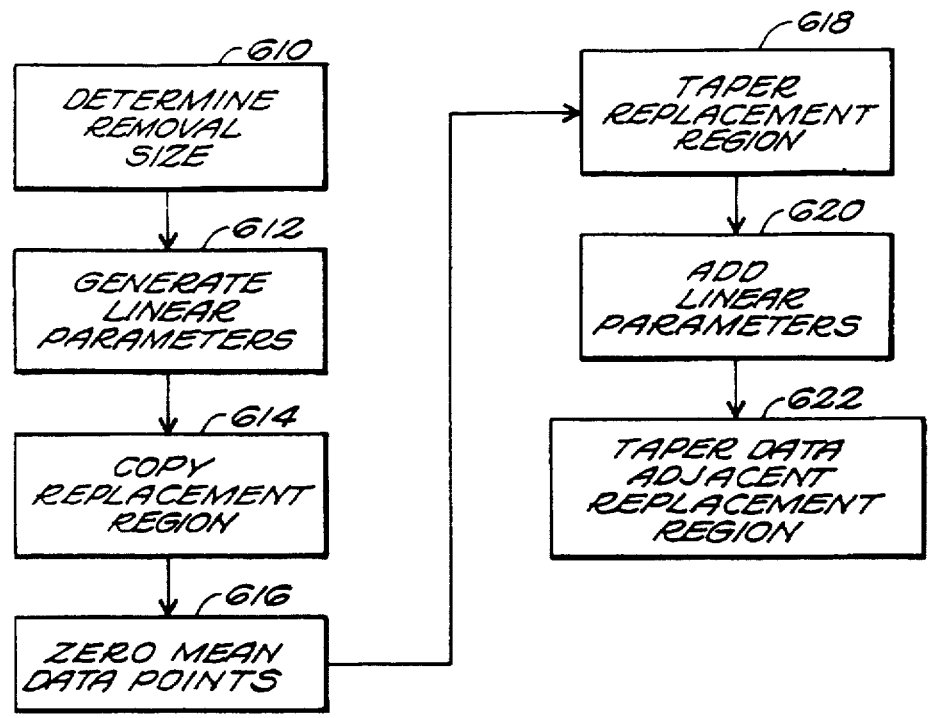
FIG. 6 shows a flow chart illustrating the process used by the spike remover shown in FIG. 2 to remove ECG and pacer artifacts from the EEG signal.
Figure 7A:
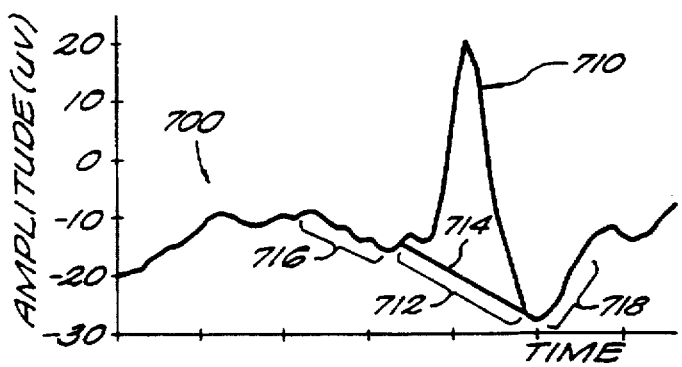
FIGS. 7 A-H show graphs of amplitude versus time of signals that illustrate the operation of mover shown in FIG. 2.

FIG. 6 shows a flow chart 600 that illustrates one preferred method that spike remover 224 may use to generate portions of the filtered signal corresponding to portions of the EEG signal 110, including ECG or pacer artifacts. In step 610, spike remover 224 determines a size SZ of a removal region of the EEG signal including the artifact. FIG. 7A shows a portion of an EEG signal 700 that includes an ECG artifact 710. As has been discussed above, ECG spike detector 220 (or pacer spike detector 222 in the case of a pacer artifact) informs spike remover 224 of the temporal location of the ECG artifact. Spike remover 224 then selects a replacement region 712 that is preferably centered about, and fully surrounds (i.e., extends before and after), the artifact 710. In one preferred embodiment, spike remover 224 selects the size SZ of the replacement region 712 to be equal to thirteen samples when the artifact is an ECG artifact and selects the size SZ to be equal to seventeen samples when the artifact is a pacer artifact. These values of thirteen and seventeen samples correspond to the average length of ECG and pacer artifacts (101.6 msec and 132.8 msec, respectively) and a sampling rate of one hundred twenty eight samples per second.

Following step 610, in step 612 spike remover 224 determines the parameters of a line (i.e., the slope m and the offset b) that connects the first and last data points in the removal region 712. FIG. 7A shows the line 714 connecting the first and last data points in the removal region 712. The epoch of data points including the artifact 710 includes data points $x_i$ for all integers i from one to N, and the artifact 710 is centered around a data point $x_p$. Spike remover 224 selects the removal region 712 so that it is centered around data point $x_p$, and since the removal region includes SZ samples, the removal region extends from data points $X_{p-(SZ-1)/2}$ to $X_{p+(SZ-1)/2}$. Spike remover 224 may generate the slope m and offset b of line 714 according to the following Equation (9).

$$m = \left( \frac{x_{p+\frac{SZ-1}{2}} - x_{p-\frac{SZ-1}{2}}}{SZ-1} \right) \quad (9)$$

$$b = x_{p-\frac{SZ-1}{2}} - m\left(p - \frac{SZ-1}{2}\right)$$

Figure 7B:
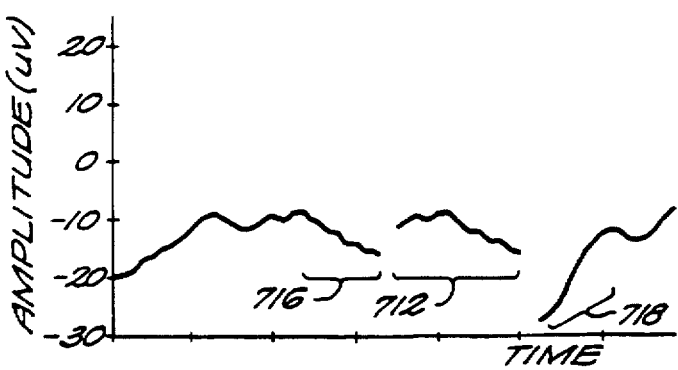

Following step 612, in step 614 spike remover 224 saves the first and last data points in the removal region 712 as $x_{first}$ and $x_{last}$, respectively, and then copies all the data points from a region 716 that precedes and is temporally adjacent the replacement region 712 into the replacement region. FIG. 7B illustrates the results of copying the data points in region 716 into the replacement region 712. As shown in FIG. 7B, following step 614 the data in the replacement region 712 is typically not continuous with the data in the region 716 preceding the replacement region 712 and with the data in a region 718 following the removal region 712. Spike remover 224 may execute step 614 according to the following Equation (10).

$$x_{first} = x_{p-\frac{SZ-1}{2}} \quad (10)$$

$$x_{last} = x_{p+\frac{SZ-1}{2}}$$

$$x\_r_i = x_{i-SZ}$$

where $$i = p - \frac{SZ-1}{2}, p - \frac{SZ-1}{2} + 1, \ldots, p + \frac{SZ-1}{2}$$

Figure 7C:
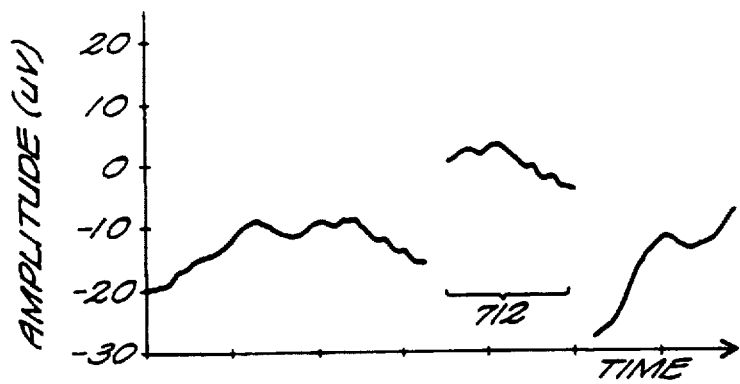

In the above Equation (10), the data points $x\_r_i$ represent the data points copied into the replacement region 712. Following step 614, in step 616 spike remover 224 replaces the data points $x\_r_i$ copied into replacement region 712 with zero mean data points $\hat{x}_i$ as is illustrated in FIG. 7C. Spike remover 224 may execute step 616 by generating the mean $\overline{x\_r}$ and by then subtracting the mean from every data point $x\_r_i$ to generate the zero mean data points $\hat{x}_i$ according to the following Equation (11).

$$\overline{x\_r} = \frac{1}{SZ} \sum_{i=p-\frac{SZ-1}{2}}^{p+\frac{SZ-1}{2}} x\_r_i \quad (11)$$

$$\hat{x}_i = x\_r_i - \overline{x\_r} \text{ for all } i \text{ from } p - \frac{SZ-1}{2} \text{ to } p + \frac{SZ-1}{2}$$

Figure 7D:
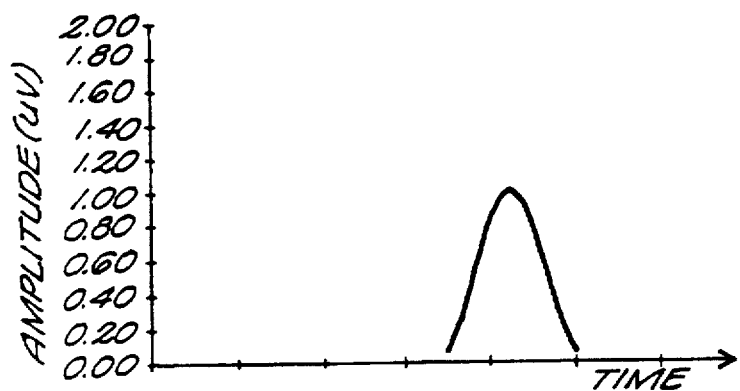

Following step 616, in step 618 spike remover 224 tapers the edges of the data points in the replacement region 712, preferably by multiplying the zero mean data points $\hat{x}_i$ in the replacement region 712 by a Hanning spectral window, an example of a Hanning spectral window being illustrated in FIG. 7D. The Hanning spectral window may be defined by a set of data points $w\_han_j$ for all integers j from one to SZ, where the data points $w\_han_j$ are given by the following Equation (12).

$$w\_han_j = 0.5\left(1 - \cos\left(\frac{2\pi(j-1)}{(SZ-1)}\right)\right) \quad (12)$$

Figure 7E:
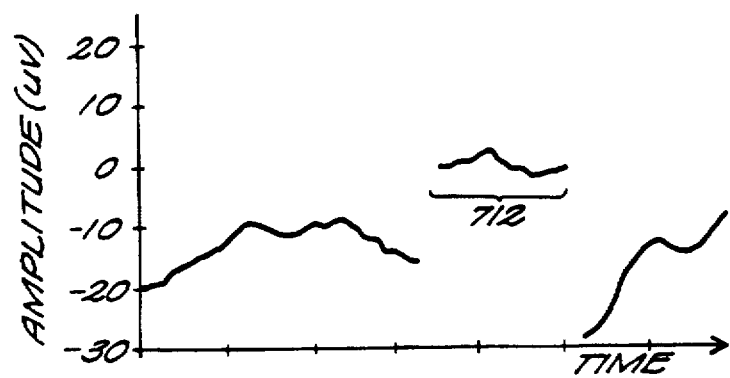

Such Hanning spectral windows are described in detail in, for example, W. H. Press, S. A. Teukolsky, W. T. Vetterling, B. P. Flannery, Numerical Recipes in C, Cambridge University Press, New York, N.Y., 1992, pg. 554. Spike remover 224 may multiply the Hanning spectral window by the zero mean data points to generate a set of tapered data points x_taper$_i$ according to the following Equation (13), the tapered data points x_taper$_i$ being illustrated in FIG. 7E.

$$x\_taper_i = \hat{x}_i w\_han_j \quad (13)$$
where
$$i = p - \frac{SZ-1}{2}, p - \frac{SZ-1}{2} + 1, \ldots, p + \frac{SZ-1}{2}$$
$$j = i - p + \frac{SZ-1}{2} + 1$$

Figure 7F:
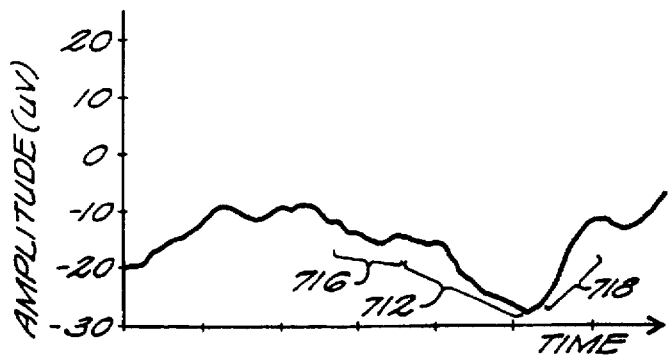

Following step 618, in step 620 spike remover 224 linearly shifts the tapered data points x_taper$_i$ in the replacement region 712 by an amount determined by the line segment 714 (shown in FIG. 7A) that was measured during step 612 and thereby generates a set of new data points x_new$_i$. As described earlier, the new ECG/Pacer artifact free data points x_new$_i$ replace the original data points x$_i$ for all i=p−(SZ−1)/2 to p+(SZ−1)/2. The result of this linear shifting of the replacement region 712 is shown in FIG. 7F. Spike remover 224 may execute step 620 according to the following Equation (14) for all i from p−(SZ−1)/2 to p+(SZ−1)/2.

$$x\_new_i = x\_taper_i + mi + b \quad (14)$$

As shown in FIG. 7F, the new data points x_new$_i$ in the replacement region 712 are continuous with the data in the regions 716 and 718 that immediately precede and follow, respectively, the replacement region. However, the transitions between regions 716 and 712 and between regions 712 and 718 are not smooth.

Figure 7G:
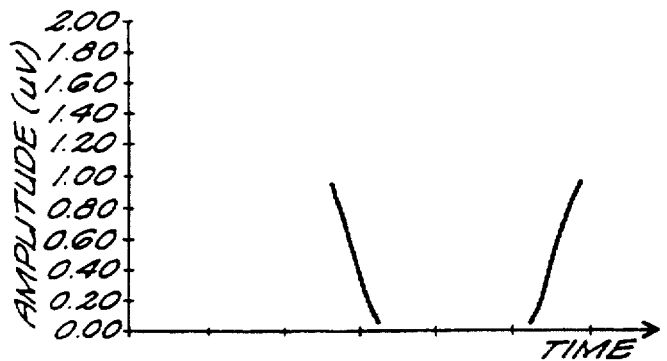
Figure 7H:
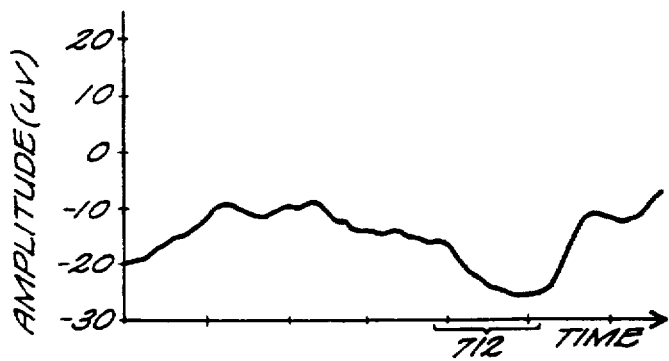

Following step 620, in step 622 spike remover 224 tapers the data at the right end of region 716 and at the left end of region 718 so that the transitions between these regions and the removal region 712 become both smooth and continuous. The results of this tapering operation are shown in FIG. 7H. One way to accomplish this tapering is to multiply the data points in the right half of region 716 by the right half of a Hanning window, and to multiply the data points in the left half of region 718 by the left half of a Hanning window as shown in FIG. 7G. Spike remover 224 may accomplish this tapering operation according to the following Equation (15).

For the left edge:
$$x\_left_i = (x_i - x_{first})w\_han_j + x_{first} \quad (15)$$
where $i = p - SZ + k$ $$j = \frac{(SZ-1)}{2} + 1 - k$$

$$k = 0, 1, 2, \ldots \frac{(SZ-1)}{2}$$

For the right edge:
$$x\_right_i = (x_i - x_{last})w\_han_j + x_{last}$$
where $i = p + SZ - k$ -continued
$$j = \frac{(SZ-1)}{2} + 1 + k$$

$$k = \frac{(SZ-1)}{2}, \frac{(SZ-1)}{2} - 1, \frac{(SZ-1)}{2} - 2, \ldots 0$$

The data points x_left$_i$ and x_right$_i$ replace the original data points x$_i$ where i is as defined above in Equation (15).

Figure 3F:
Figure 5E:
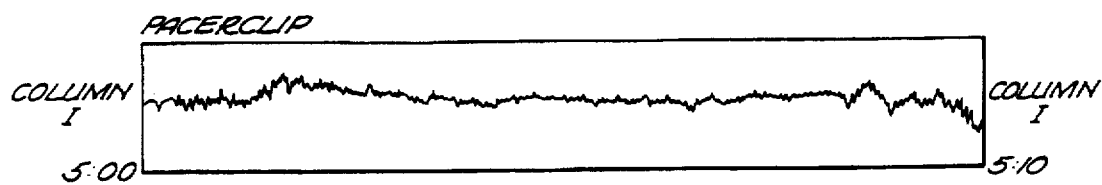

In summary, ECG and pacer artifact filter 120 (shown in FIG. 2) removes data in regions of the EEG signal 110 that include ECG or pacer artifacts and replaces the data in those removed regions with data from a region temporally adjacent (and preferably preceding) the removed region. Filter 120 also preferably tapers the data at the beginning and end of the removed regions and also tapers the data at the ends of the regions preceding removed regions and also tapers the data at the beginnings of regions following the removed regions so that the data in the removed regions connects smoothly with the data in regions preceding and following the removed regions. FIG. 3F shows a filtered signal generated by filter 120 in response to the EEG signal shown in FIG. 3A. As shown, the ECG artifacts present in the signal shown in FIG. 3A have been smoothly removed from the signal shown in FIG. 3F. Similarly, FIG. 5E shows a filtered signal generated by filter 120 in response to the EEG signal shown in FIG. 5A. As shown, the pacer artifacts present in the signal shown in FIG. 5A have been smoothly removed from the signal shown in FIG. 5E. One preferred method of replacing and tapering the data has been discussed above in connection with FIGS. 6 and 7A–7H, although those skilled in the art will appreciate that filter 120 may operate in different fashions as well. For example, the data which is copied into the replacement region may come from a second EEG signal which is artifact free. Preferably, filter 120 removes and tapers the data in ways that do not significantly alter the spectral content of the EEG signal.

Figure 8:
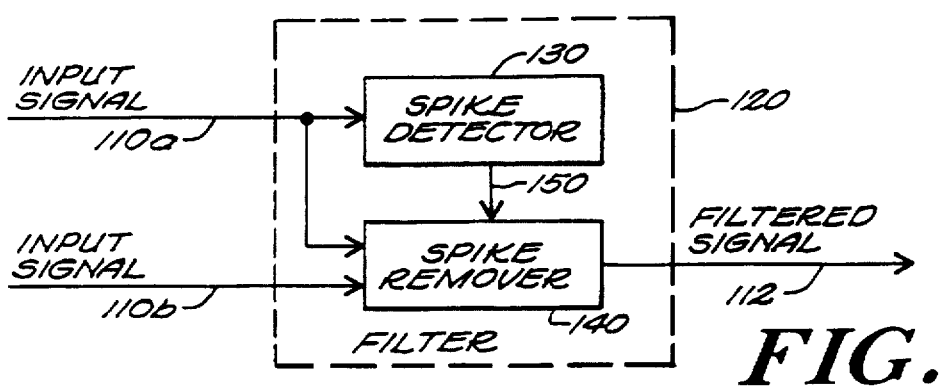
FIG. 8 shows a block diagram of another embodiment of a filter constructed according to the invention.

FIG. 8 shows a block diagram of another embodiment of filter 120. In this embodiment, filter 120 receives two input signals 110a, 110b representative of cerebral activity and generates therefrom the filtered signal 112. The input signals 110a, 110b may represent, for example, EEG signals from two different channels of an EEG processor. In this embodiment, the first input signal 110a is applied to both the spike detector 130 and the spike remover 140, and the second input signal 110b is applied to only the spike remover 140.

In operation, when there are no artifacts present in the input signal 110a (as indicated by the output signal 150 of spike detector 130), the filter 120 generates the filtered signal 112 so that it is substantially equal to the first input signal 110a. When there is an artifact present in the first input signal 110a (as indicated by the output signal 150), the filter 120 generates the corresponding portion of the filtered signal using data from the second (preferably artifact free) input signal 110b. This embodiment may be particularly useful for systems that normally monitor several different channels of EEG signals. Filter 120 may for example select the channel containing the lowest amount of artifacts to use as the source of the second input signal 110b. As discussed above, spike detector 130 may be configured to detect cardiac artifacts such as ECG or pacer artifacts. Alternatively, spike detector 130 may be configured to detect any type of artifacts characterized by "spike" like shapes.

In summary, digital embodiments of filter 120 generate a digital filtered signal corresponding to a digital input signal. When the input signal does not include an artifact, filter 120 generates data points of the filtered signal so that they are substantially equal to corresponding data points of the input signal. When the input signal does include an artifact, filter 120 generates data points of the filtered signal so that they are substantially equal to data points from a portion of the input signal temporally adjacent the portion of the input signal including the artifact, or so that they are substantially equal to data points from another input signal. Filter 120 of course also applied filtering as discussed above to smooth portions of the filtered signal corresponding to portions of the input signal that included an artifact so data in the replacement regions connects smoothly with adjacent portions of the signal.

Filter 120 (shown in FIG. 2) has been discussed in terms of a digital implementation. Those skilled in the art will appreciate that various components of filter 120 (e.g., high pass filter 210 as shown in FIG. 2) may be implemented using discrete hardware modules, or alternatively, may be implemented using software executed by a digital computer. In other embodiments, some components of filter 120 (e.g., high pass filter 210) may be implemented using analog devices. Further, filter 120 has been discussed for convenience as being partitioned into separate modules (e.g., high pass filter 210 and band pass filter 214), however, those skilled in the art will appreciate that these divisions have been presented merely for convenience of exposition, and filter 120 may be partitioned in different ways without departing from the scope of the invention, and all of filter 120 may be implemented as a single module that is implemented, for example, as software executed by a digital computer.

Since certain changes may be made in the above apparatus without departing from the scope of the invention herein involved, it is intended that all matter contained in the above description or shown in the accompanying drawing shall be interpreted in an illustrative and not a limiting sense.

We claim:

1. A system for processing a signal representative of cerebral activity, said signal including at least one cardiac artifact, the system comprising:
   means for identifying a first region and a second region of said signal, said first region including one of said cardiac artifacts, said second region being temporally adjacent said first region;
   means for copying said second region of said signal into said first region of said signal.

2. A system according to claim 1, wherein said second region precedes said first region.

3. A system according to claim 1, further including means for suppressing discontinuities between said first and second regions.

4. A system according to claim 1, further including means for smoothly connecting said first and second regions.

5. A system according to claim 1, wherein said signal is an EEG signal.

6. A system according to claim 1, wherein said artifact in said first region is an ECG artifact.

7. A system according to claim 1, wherein said artifact in said first region is a pacer artifact.

8. An artifact reduction filter for processing an input signal representative of cerebral activity, a first interval of said input signal being substantially free of cardiac artifacts, a second interval of said input signal including a cardiac artifact, said artifact reduction filter generating a reduced artifact output signal, said reduced artifact output signal including a first interval corresponding temporally to said first interval of said input signal and including a second interval corresponding temporally to said second interval of said input signal, said artifact reduction filter using said first interval of said input signal to generate said first interval of said reduced artifact output signal, said artifact reduction filter using a portion of said input signal other than said second interval to generate said second interval of said reduced artifact output signal.

9. An artifact reduction filter according to claim 8, wherein said portion of said input signal other than said second interval comprises a portion of said input signal temporally adjacent said second interval.

10. An artifact reduction filter according to claim 9, wherein said portion of said input signal other than said second interval comprises a portion of said first interval of said input signal.

11. An artifact reduction filter according to claim 8, further comprising a smoothing filter for smoothing an intersection between said first and second intervals of said reduced artifact output signal.

12. An artifact reduction filter according to claim 8, further comprising an artifact detection filter, said artifact detection filter receiving said input signal and generating therefrom an artifact location signal representative of a temporal location of said cardiac artifact in said input signal.

13. An artifact reduction filter according to claim 12, further comprising an artifact removing filter, said artifact removing filter receiving said input signal and said artifact location signal and generating therefrom said reduced artifact output signal.

14. A filter for receiving and processing first and second input signals primarily representative of cerebral activity, a first interval of said first input signal being substantially free of cardiac artifacts, a second interval of said first input signal including a cardiac artifact, said filter generating a reduced artifact output signal, said reduced artifact output signal including a first interval temporally corresponding to said first interval of said first input signal and a second interval temporally corresponding to said second interval of said first input signal, said filter using said first interval of said first input signal to generate said first interval of said reduced artifact output signal, said filter using a portion of said second input signal to generate said second interval of said output signal.

15. A method of generating a reduced artifact output signal from an input signal representative of cerebral activity comprising:
   using the input signal to generate the reduced artifact output signal when the input signal does not include a cardiac artifact;
   using a portion of the input signal distinct from the cardiac artifact to generate the reduced artifact output signal when the input signal does include a cardiac artifact.

16. A method of generating a reduced artifact output signal from a first input signal primarily representative of cerebral activity and a second input signal primarily representative of cerebral activity comprising:
   using the first input signal to generate the reduced artifact output signal when the first input signal does not include a cardiac artifact;

using a portion of the second input signal to generate the reduced artifact output signal when the first input signal does include a cardiac artifact.

17. A filter according to claim 14, wherein said first and second input signals are EEG signals.

18. A filter according to claim 14, wherein said first input signal is generated in response to a signal generated by an EEG electrode.

19. A filter according to claim 14, wherein said filter uses said second input signal and not said first input signal to generate said second interval of said output signal.

20. A method according to claim 16, wherein said first and second input signals are EEG signals.

21. A method according to claim 16, wherein said first input signal is generated in response to a signal generated by an EEG electrode.

22. A method according to claim 16, wherein using a portion of the second input signal to generate the reduced artifact output signal when the first input signal does include a cardiac artifact comprises using the second input signal and not the first input signal.

* * * * *